(12) United States Patent
Brinz et al.

(10) Patent No.: US 7,448,279 B2
(45) Date of Patent: Nov. 11, 2008

(54) DEVICE FOR TESTING MATERIAL PROPERTIES WITH REGARD TO COMBINED TENSILE AND SHEAR LOADS, IN PARTICULAR FOR TESTING ADHESIVES

(75) Inventors: Thomas Brinz, Bissingen A.D. Teck (DE); Jane Lewis, Stuttgart (DE); Thomas Geiger, Walddorfhaeslach (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 11/073,103

(22) Filed: Mar. 3, 2005

(65) Prior Publication Data

US 2005/0193829 A1 Sep. 8, 2005

(30) Foreign Application Priority Data

Mar. 6, 2004 (DE) .................. 10 2004 011 099

(51) Int. Cl.
*G01N 3/24* (2006.01)
(52) U.S. Cl. .................. 73/841; 73/150 A; 73/827; 73/842
(58) Field of Classification Search ............ 73/827, 73/841, 842, 150 A
See application file for complete search history.

(56) References Cited

U.S. PATENT DOCUMENTS

| | | | | |
|---|---|---|---|---|
| 3,186,221 A | * | 6/1965 | Steib ................ | 73/150 A |
| 4,878,978 A | * | 11/1989 | Goel et al. ............. | 156/272.4 |
| 5,033,309 A | * | 7/1991 | Wycherley et al. ........... | 73/842 |
| 5,906,766 A | * | 5/1999 | Chaffin ................ | 219/765 |
| 6,619,358 B2 | * | 9/2003 | Murphy ................ | 156/359 |
| 6,777,668 B2 | * | 8/2004 | Krieg et al. ................ | 250/239 |
| 6,813,958 B2 | * | 11/2004 | Crosby et al. ................ | 73/800 |
| 2002/0194930 A1 | * | 12/2002 | Crosby et al. ................ | 73/827 |

FOREIGN PATENT DOCUMENTS

DE     196 44 094     11/1997

* cited by examiner

*Primary Examiner*—Edward Lefkowitz
*Assistant Examiner*—Freddie Kirkland, III
(74) *Attorney, Agent, or Firm*—Kenyon & Kenyon LLP

(57) ABSTRACT

A device for testing material properties with regard to combined tensile and shear loads, in particular for testing adhesives, includes a device for applying the force, a measuring device, a test piece receptacle, and a test piece having a bonding surface. The test piece is dimensionally stable within the intended limits of the force to be applied. This measure ensures that the shear forces acting on the joint act approximately at a right angle to the bonding surface over the entire test period, so that realistic conclusions may be drawn with regard to the material properties of the tested adhesive.

13 Claims, 2 Drawing Sheets

DEVICE FOR TESTING MATERIAL PROPERTIES WITH REGARD TO COMBINED TENSILE AND SHEAR LOADS, IN PARTICULAR FOR TESTING ADHESIVES

BACKGROUND INFORMATION

Different methods and devices are used for characterizing adhesives. The most common test is the combined tensile and shear test. Two standard test strips are bonded together as test pieces and are pulled apart after hardening of the adhesive. The measured force up to the breaking point of the joint is a measure for the adhesive strength. This test is easily performed; however, due to the asymmetrical tensile load, twisting of the joint along the action of the force occurs in the two test strips. The tensile force no longer acts on the bonding surface at a right angle, which makes it impossible to draw an unambiguous conclusion about the adhesive's tensile properties.

A material which is mechanically stronger than the test strips is used in an approach known as the "thick combined tensile and shear test." For forming a test piece, two oblong strips having a sufficient thickness and width are bonded on top of one another over the entire surface. Subsequent to bonding, both strips must be cut through perpendicularly to the longitudinal axis of the test piece in such a way that a defined friction-locked bonding joint is created between the cut-off points. When cutting, attention must be paid that the second test strip bonded to the particular test strip is not damaged.

Providing a test piece is thus highly complex and has the additional disadvantage that the accuracy in determining the effective bonding surface is dependent on the accuracy in creating the cut-off points in the individual test strips.

However, in very strong adhesive joints it may occur that the test strips have a lower mechanical strength than the bonding joint to be tested and break.

The availability of test pieces is thus highly dependent on the properties of the adhesive to be tested. In particular adhesives having high adhesive forces demand a correspondingly great preparation effort.

The plurality of tests for determining the desired properties of an adhesive to be performed in combinatorial chemistry is time-consuming, expensive, and associated with unsatisfactory test accuracy.

SUMMARY OF THE INVENTION

A test piece, which has a dimensionally stable design within the limits of the intended force to be applied, is provided for the device for testing material properties regarding combined tensile and shear loads, in particular for testing adhesives. This ensures that the shear forces acting on the joint act approximately at a right angle to the bonding surface over the entire test period. Realistic conclusions with regard to the material properties of the tested adhesive may be drawn on this basis.

The previously known problem of twisting and displacement of the bonding surface with regard to the force flux direction due to the previously used test strips is thus eliminated.

In an advantageous embodiment of the present invention, the test piece is made of a material permeable to electromagnetic waves. This has the advantage that the adhesive applied to the bonding surface may be acted upon from the outside as well as from the side of the bonding surfaces, i.e., in the areas which were previously inaccessible for subsequent force application. In this way, hardening of the adhesive may be influenced by supplying energy in the form of electromagnetic waves. Testing of the adhesive may thus be performed from the still totally unbonded state to the totally hardened state depending on the parameter that is to be determined.

Moreover, in an advantageous embodiment an energy source for generating electromagnetic waves for utilizing the above-mentioned advantages may be provided. Examples of such energy sources include infrared sources, UV sources, high-frequency sources, possibly also an electric power source for conducting an electric current through the adhesive joint, and the like, as well as sources for convection heat.

Moreover, in an advantageous embodiment at least one further test piece may be placed on the device, so that different adhesive compositions, which are each applied to a particular test piece, may be tested in a single testing operation.

In another embodiment the test pieces may be situated in such a way that their bonding surfaces face each other. This makes it possible to apply the adhesive to be tested between two front faces of the test pieces for example and subject it to the testing method. In a possible arrangement of multiple test pieces next to one another, an entire matrix of multiple rows and columns may be created, for example, resulting in further efficiency improvement during the course of the test.

In a particularly advantageous embodiment the test pieces may be adjustable in a plane oriented approximately parallel to their bonding surfaces. This makes it possible to subject one test piece after another from the above-mentioned matrix to the testing method.

A further advantage of the present invention arises from the fact that the size of the bonding surface is defined by the contour of a surface of test piece 5. This is the result, for example, when the test piece has an approximately cylindrical shape, the front face being provided as the bonding surface. Of course, the test piece may also have a rectangular, square, triangular, or a differently shaped base surface. The shape of the surface is only important to the effect that it accurately defines the size of the surface which is the basis for deriving the accurate material properties of the adhesive to be tested.

In an additional advantageous embodiment the device for applying the force may be designed for exerting a combined compression-shear force on the adhesive. This makes it possible to determine further parameters of the adhesive to be tested.

In a further advantageous embodiment the device for applying the force may be designed for exerting front face pulling forces and/or torsional forces on the adhesive.

A particularly advantageous embodiment may have a device for applying the force which is designed for exerting a static and/or dynamic force on the adhesive. These embodiments make it possible to simulate a great variety of realistic loads on the adhesive.

Shear, tensile, compression, and torsion loads may be simulated, but it is also possible to apply them in the form of static as well as dynamic loads. This results in a test spectrum from a permanent static continuous load to a constantly changing load pattern, including high oscillations.

In a further advantageous embodiment the device for applying the force operates as a function of the path or the force. This makes it possible to compress the adhesive to a certain height and to subsequently test its properties. Depending on the requirement, the height may be adjusted via a variable pressure with respect to a targeted longitudinal expansion or via a variable path with respect to a certain exerted pressure.

For receiving the test pieces, in an advantageous embodiment the test piece and the receptacle may be connected in a friction-locked and/or a form-fitted manner and/or via a clamping device. This makes it possible to transfer tensile, compression, and rotational motions without play. Rapid clamping of the test pieces is also possible in a hydraulically or pneumatically operated clamping device. Of course, other means for operating the clamping device are also conceivable.

Moreover, in an advantageous embodiment an adhesive application device may be present in order to automate the application of the adhesive.

DETAILED DESCRIPTION

Figure 1:
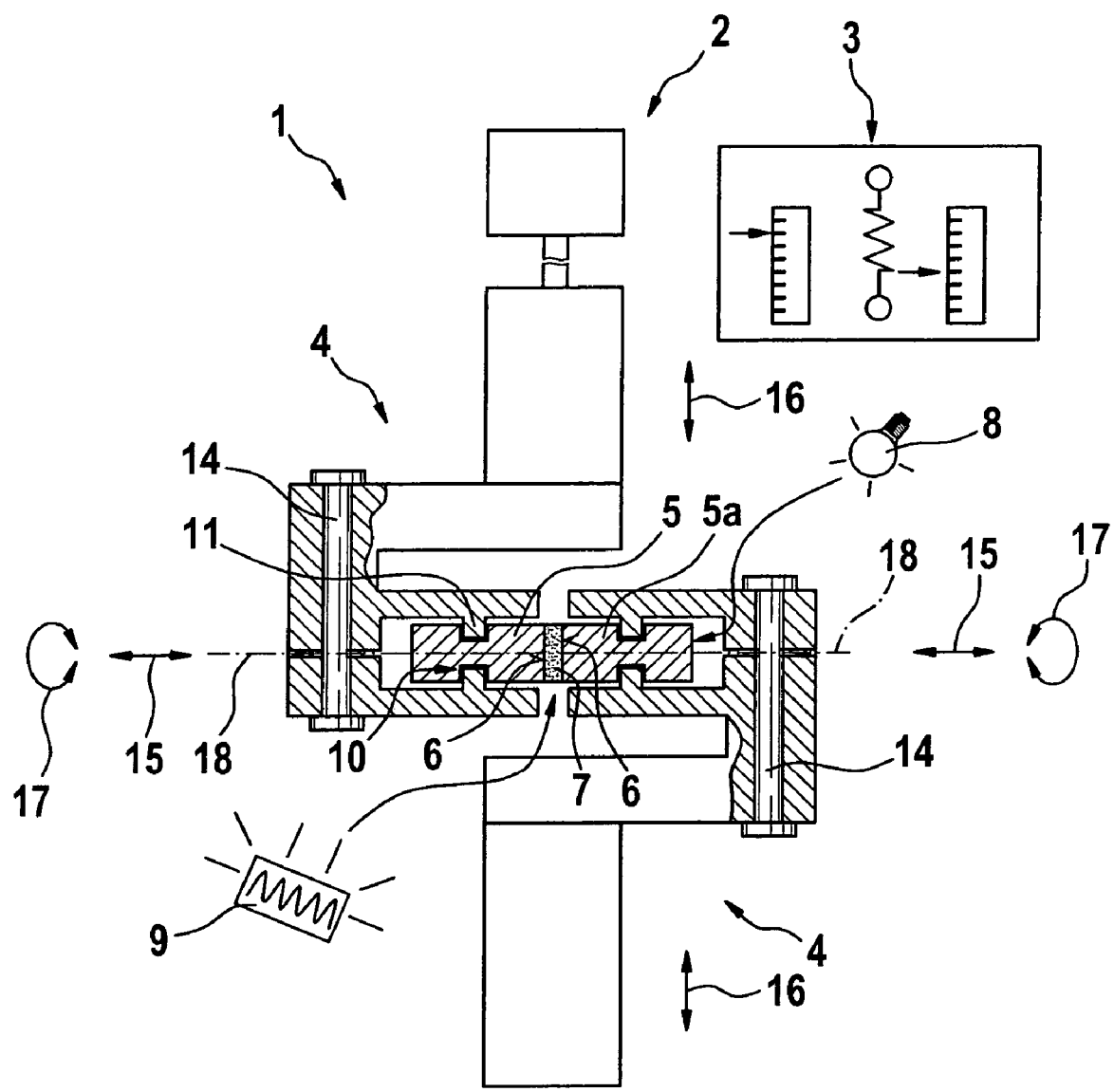
FIG. 1 shows a symbolic sectional representation of sections of units of a device for testing material properties with regard to combined tensile and shear loads, including test piece receptacles and test pieces situated therein, bonded by an adhesive.

FIG. 1 shows a device 1 for testing material properties with regard to combined tensile and shear loads, in particular for testing adhesives. This device has a device 2 for applying the force and a measuring device 3. Test pieces 5, 5a are fixed on device 1 via test piece receptacles 4. Bonding surfaces 6 are formed on the front faces of the test pieces and are bonded by adhesive 7 to be tested.

Test pieces 5, 5a are made of a material permeable to electromagnetic waves, so that the electromagnetic waves exiting from the respective sources are able to act on the adhesive to be tested from each side. A UV light source 8 and, as another example, a heat source 9 are depicted as sources. Depending on the embodiment, the source for heat supply may be situated directly in the area of the joint or at a suitable radiation entry point for the UV light. A properly conducting connection from the respective source to the joint or to the wave entry point may also be present, so that the source may be situated at a protected place.

Test pieces 5 have recesses 10 into which corresponding pickups 11 of test piece receptacle 4 engage. This makes it possible to apply a force to test pieces 5 axially.

Figure 3:
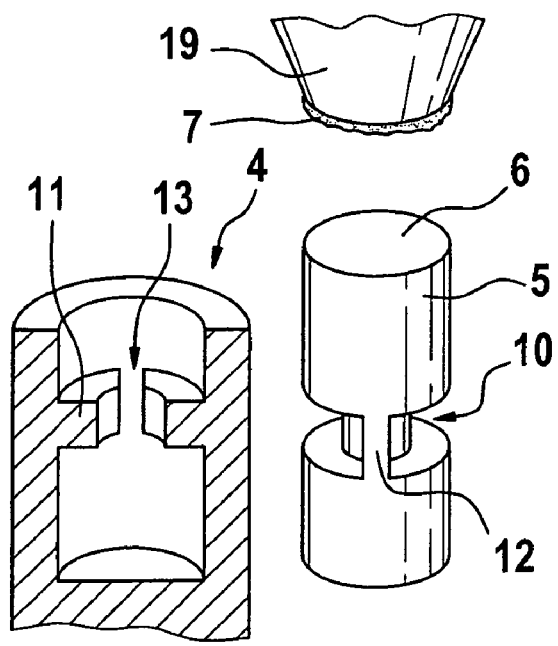
FIG. 3 shows, in contrast to embodiment 2, a modified embodiment of a test piece and a corresponding test piece receptacle, as well as an adhesive application device in a sectional view.

In order to also transfer a rotational motion to the test pieces, in a particular embodiment recesses 10 have catches 12 which engage in recesses 13 in test piece receptacles 4 (see FIG. 3).

Clamping devices 14 are provided for fixing test pieces 5 in test piece receptacles 4 in a friction-locked manner.

In the present case, test piece 5 together with an additional test piece 5a is used for testing the adhesive. For the sake of simpler illustration, the three directions of movement in which device 2 for applying the force may propel test pieces 5, 5a and correspondingly adhesive 7 to be tested are depicted by three arrow directions 15, 16, and 17. For exerting forces in certain directions on test pieces 5, 5a, the embodiment of test piece receptacles 4 may possibly deviate from the symbolically illustrated embodiment.

The directions of movement corresponding to arrow directions 15, 16, and 17 refer to axis 18 running through test pieces 5, 5a and adhesive 7. Thus, this is a pure function representation of an exemplary embodiment.

Figure 2:
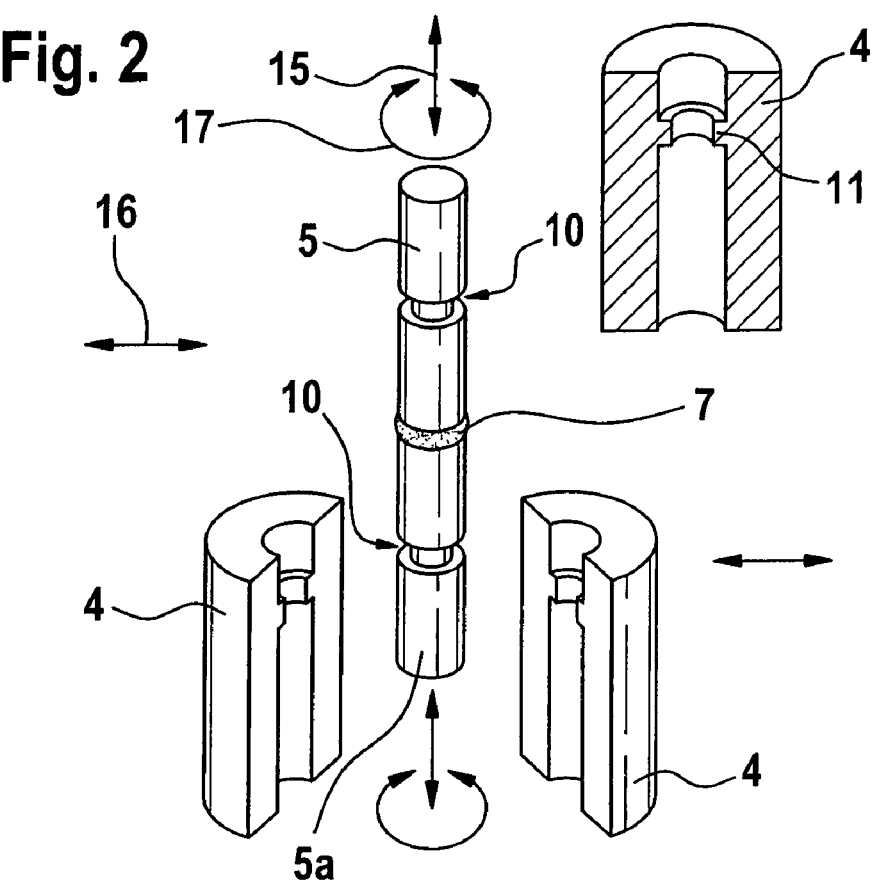
FIG. 2 shows an oblique top view of two test pieces bonded by an adhesive, and test piece receptacles situated alongside in a sectional view.

In FIG. 2, two test pieces 5, 5a are bonded on their front faces using adhesive 7. Left and right of test piece 5a, two halves of a test piece receptacle 4 are illustrated laterally swiveled away. A further test piece receptacle 4 is shown in an oblique top view right above test piece 5.

With regard to recess 10 and pickup 11, FIG. 3 shows an embodiment of a test piece 5 and a test piece receptacle 4 modified to the effect that they additionally have catch 12 and corresponding recess 13, whereby a rotational motion may be transferred. An adhesive application device 19, from which a certain amount of adhesive 7 protrudes in the direction of front face 6 for application, is illustrated above front face 6.

Figure 4:
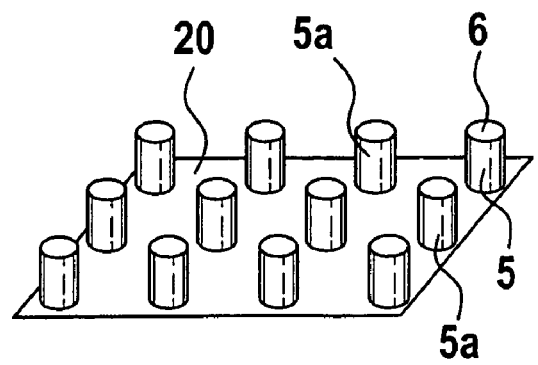
FIG. 4 shows a matrix of test pieces situated side by side.

FIG. 4 shows a matrix-like arrangement of test pieces 5, 5a having a row of three and a column of four test pieces 5, 5a. These are situated in an upright position in a plane 20 which is oriented parallel to bonding surface 6 and in which, in a particular embodiment, test pieces 5, 5a are displaceable for improving the efficiency of the testing operation.

A plurality of different testing operations, such as tensile, compression, combined torsion-shear tests and also tests with regard to surface adhesion and peeling stability, may basically be performed using the device according to the present invention. The illustrated embodiments are in no way intended to be restricting but rather as examples and include all design possibilities within the scope of the claims.

What is claimed is:

1. A device for testing material properties with regard to combined tensile and shear loads, comprising:
    a device adapted to apply a force including tensile and shear components;
    a measuring device;
    a test piece receptacle;
    a test piece having a bonding surface, the test piece being dimensionally stable within intended limits of the force to be applied; and
    at least one additional test piece situated on the device;
    wherein a matrix-like arrangement of test pieces with bonding surfaces is provided, the test pieces adjustable together in a plane oriented substantially parallel to the bonding surfaces, the test pieces having different adhesive compositions.

2. The device according to claim 1, wherein the device is for testing adhesives.

3. The device according to claim 2, wherein the device for applying the force exerts a combined compression-shear force on an adhesive.

4. The device according to claim 2, wherein the device for applying the force exerts a front face pulling force on an adhesive.

5. The device according to claim 2, wherein the device for applying the force exerts a torsional force on an adhesive.

6. The device according to claim 2, wherein the device for applying the force exerts at least one of a static and a dynamic force on an adhesive.

7. The device according to claim 1, wherein at least one test piece is composed of a material permeable to electromagnetic waves.

8. The device according to claim 1, further comprising an energy source for generating electromagnetic waves.

9. The device according to claim 1, wherein at least one of (a) the test pieces are situated in such a way that their bonding surfaces face each other and (b) the test pieces are situated side by side.

10. The device according to claim 1, wherein a size of the-bonding surface is defined by a contour of a surface of at least one test piece.

11. The device according to claim 1, wherein the device for applying the force operates as a function of at least one of a path and the force.

12. The device according to claim 1, wherein the test piece receptacle has at least one of a friction-locked and a form-locked connection to at least one of at least one test piece and a clamping device.

13. A device for testing material properties with regard to combined tensile and shear loads, comprising:
- a device adapted to apply a force including tensile and shear components;
- an energy source for generating electromagnetic waves;
- a measuring device;
- a test piece receptacle; and
- a test piece having a bonding surface, the test piece being dimensionally stable within intended limits of the force to be applied and composed of a material permeable to the electromagnetic waves.

* * * * *